United States Patent [19]

Arunachalam et al.

[11] Patent Number: 5,295,084
[45] Date of Patent: Mar. 15, 1994

[54] VIBRATING TUBE DENSIMETER

[75] Inventors: Palani Arunachalam; Robert Bruck; David S. McCollum, all of Boulder, Colo.; Joseph D. Titlow, Palos Verdes Estates, Calif.

[73] Assignee: MicroMotion, Inc., Boulder, Colo.

[21] Appl. No.: 773,200

[22] Filed: Oct. 8, 1991

[51] Int. Cl.$^5$ .............................. G01N 9/00
[52] U.S. Cl. ................... 364/558; 364/510; 73/32 A; 73/861.37
[58] Field of Search ............ 73/861.37, 32 A; 364/558, 510

[56] References Cited

U.S. PATENT DOCUMENTS

| 4,240,285 | 12/1980 | Langdon | 73/32 A |
| 4,470,294 | 9/1984 | Hamel | 73/861.37 |
| 4,491,009 | 1/1985 | Ruesch | 73/32 A |
| 4,843,890 | 7/1989 | Samson et al. | 364/510 |
| 4,876,879 | 10/1989 | Ruesch | 73/32 A |
| 5,044,207 | 9/1991 | Atkinson et al. | 73/861.37 |

OTHER PUBLICATIONS

William Ross Hamel, "Analysis of a Cantilever Coriolis Mass Flowmeter Concept" Dec. 1981, A Dissertation Presented for the Doctor of Philosophy Degree, The University of Tennessee, Knoxville.
G. W. Housner; "Bending Vibrations of a Pipe Line Containing Flowing Fluid"; Jun., 1952; pp. 205-208. Journal of Applied Mechanics.
R. H. Long, Jr.; "Experimental and Theoretical Study of Transverse Vibration of a Tube Containing Flowing Fluid"; Mar., 1955; pp. 65-68. Journal of Applied Mechanics.
S. Naguleswaran and C. H. J. Williams; "Lateral Vibration of a Pipe Conveying a Fluid"; vol. 10, No. 3, no month, 1968; pp. 228-238. Journal Mechanical Engineering Sciences.

Primary Examiner—Jack B. Harvey
Assistant Examiner—Jae H. Choi
Attorney, Agent, or Firm—Duft, Graziano & Forest

[57] ABSTRACT

A Coriolis effect densimeter which produces density output data of improved accuracy by embodying the principal that the natural frequency of a vibrating tube filled with material decreases with an increase in the material mass flow rate. High accuracy output data is achieved by measuring the natural frequency of the tube as material flows therethrough, correcting the measured frequency to compensate for the decrease in natural frequency caused the material flow (mass flow rate) and using the corrected natural frequency in the material density computation.

54 Claims, 5 Drawing Sheets

FIG. I.

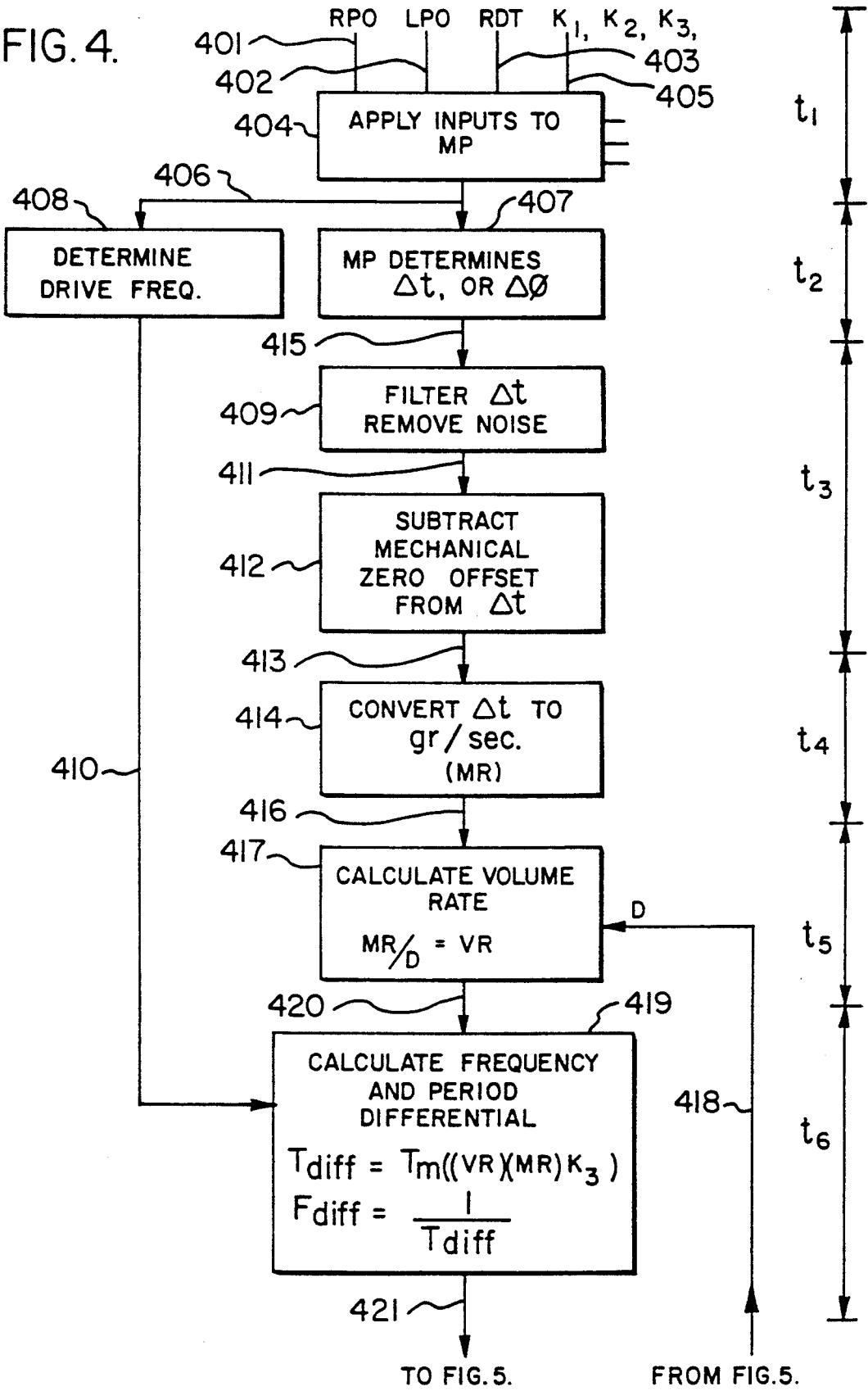

VIBRATING TUBE DENSIMETER

FIELD OF THE INVENTION

This invention relates to a vibrating tube flowmeter and, more particularly, to a Coriolis mass flowmeter that provides density output data of increased accuracy and has an increased range of operation.

PROBLEM—BACKGROUND OF THE INVENTION

Prior Coriolis effect densimeters, such as that disclosed in the U.S. Pat. No. 4,876,879 to Ruesch of Oct. 31, 1989, were designed and operated with the assumption that the accuracy of the density measurement is not affected by changes in the mass flow rate, temperature, viscosity or pressure of the measured fluid. In particular, these densimeters were designed with the assumption that changes in the natural frequency of the driven flow tubes are only caused by changes in the density of the material flowing through the flow tube. The density measurement was determined by these meters directly from the measured natural frequency.

Each Coriolis effect densimeter has a specified set of recommended operating parameters such as temperature, mass flow rate, density, viscosity, pressure, etc. Coriolis effect meters designed in accordance with these assumptions have operated satisfactorily and given excellent results for most users when their recommended operating ranges are not exceeded. These meters then normally yield excellent performance coupled with a high precision of output data.

However, circumstances occur in which a Coriolis effect densimeter may be operated beyond its recommended operating range or near the upper limits of the recommended operating range of flow rates. Under these conditions, the accuracy of the output data is decreased somewhat as compared to the accuracy of the output data usually obtained when the meters are operated within their recommended operating ranges.

Heretofore, when a user required higher mass flow rates, she or he was required to switch to a higher capacity Coriolis meter in order to operate the flowmeter with an acceptable pressure drop. However, advances in the design of Coriolis mass flowmeters have resulted in lower pressure drops which have effectively broadened the useful range of the flowmeter. Users operating their flowmeters over this extended range, which may exceed the previously recommended range, may obtain output data that is not of the highest possible accuracy.

SOLUTION TO THE PROBLEM

The above problem is solved and an advance in the art is achieved by the present invention which permits output data of high accuracy to be obtained from Coriolis effect densimeters operating under conditions in which their heretofore recommended mass flow rate operating range is exceeded.

It is known by researchers in this field that the natural frequency of a vibrating tube of Coriolis effect densimeter is not a constant, but instead, decreases with increases in the mass flow rate of material through the vibrating tube. Even though this effect has been known, it has been disregarded by the designers of the heretofore available Coriolis effect densimeters. Possible adverse consequences of this effect were avoided by limiting the operation of each meter to the lower portion of its theoretical mass flow rate operating range, because of pressure drop concerns, wherein the effect is of negligible consequences on the accuracy of the meter output data. However, uses beyond the recommended operating range of early Coriolis meters resulted in density output data that is less accurate than the data obtained when the recommended operating ranges are followed. The reason for this is that when the recommended mass flow rate operating range is exceeded, the flowmeter is operating at a point where the decrease in natural frequency is significant. This decrease in natural frequency becomes even more significant at very high flow rates.

The problem of obtaining accurate density measurements at higher flow rates is solved by the present invention by the provision of a method and apparatus which takes into account the fact the measured natural frequency of a driven flow tube is affected by the density of the material flowing through the flow tube as well as the mass flow rate of the material. The measured natural frequency is corrected by the present invention in accordance with these factors to obtain a more accurate natural frequency determination. This corrected natural frequency is then used to measure the density of the material with high accuracy.

SUMMARY OF THE INVENTION

The heretofore available Coriolis mass flowmeters were designed and operated as described by the Ruesch patent. Experience has shown that the Ruesch-type meter works well for a limited range of mass flow rates and densities. However, it does not take into account certain characteristics of a vibrating structure that can affect the meter's accuracy when an attempt is made to expand the operating range.

A theoretical model that does consider other effects of material flow through a vibrating tube was developed by G. W. Housner in studies of the Trans-Arabia pipeline in the 1950s. This model is discussed in "Bending Vibrations of a Pipe Line Containing Flowing Fluid" by G. W. Housner, JOURNAL OF APPLIED MECHANICS, Trans. ASME, vol. 74, 1952, pp 205-208. This model is set forth in an equation derived by Housner which is a one dimensional fluid elastic equation describing the undamped, transverse, free vibration of a flow tube containing flowing material as follows:

$$EI \frac{\partial^4 u}{\partial x^4} + (\rho_f A_f + \rho_s A_s) \frac{\partial^2 u}{\partial t^2} + 2\rho_f A_f v_o \frac{\partial^2 u}{\partial x \partial t} +$$

$$\rho_f A_f v_o^2 \frac{\partial^2 u}{\partial x^2} = 0$$

where
- E = modulus of elasticity of the flow tube
- I = moment of inertia of the flow tube
- $\rho_f$ = density of the material
- $\rho_s$ = density of the flow tube
- $A_f$ = cross-sectional area of the flow region
- $A_s$ = cross-sectional area of the flow tube
- $v_o$ = flow speed
- u(x,t) = transverse displacement of the flow tube Approximate solutions to Housner's equation for some special cases reveals the following causal relationship between the natural frequency of a flow tube and the mass flow rate of fluid flowing through the tube:

$$\omega_n = \left(\frac{n\pi}{l}\right)^2 \left[\frac{EI}{\rho_f A_f + \rho_s A_s}\right]^{\frac{1}{2}} \left\{1 - v_o^2 \left(\frac{l}{n\pi}\right)^2 \frac{v}{2} \left[1 + \frac{\mu}{2(1+\mu)}\right]\right\}$$

where
n = integer
l = tube length $$v = \frac{\rho_f A_f}{EI} \quad \mu = \frac{\rho_f A_f}{\rho_s A_s}$$

High precision numerical calculations and detailed tests on actual Coriolis flowmeters have substantiated the functional relationship between natural frequency and mass flow rate given by this equation.

This effect manifests itself as a decrease in the natural frequency of the material filled flow tube as the mass flow rate increases. The only practical application of Housner's equations was directed toward establishing a critical flow velocity wherein the flow tube would experience "buckling" or other instabilities as the natural frequency decreased to zero. The mass flow rates associated with these phenomena are extremely high compared to those encountered in commercial flow metering. There has been no known application of this effect in Coriolis effect meters until the present invention.

The present invention increases the useful operating range of Coriolis effect densimeters by embodying the principal that the natural frequency of a driven flow tube decreases as the mass flow rate increases. The density measurements of prior densimeters assumed that the natural frequency of a material filled flow tube was affected only by changes in the density of the material flowing through the flow tube. However, according to the method and apparatus of the present invention, density measurements are determined not only by the density of the material flowing through the flow tube, but also are dependent upon the mass flow rate. The present invention thereby more accurately measures the density of the material at higher material mass flow rates.

The method and apparatus of the present invention determines the amount by which the natural frequency of a driven flow tube is decreased because of increases in the material mass flow rate of the tube. This frequency change information is used to generate a corrected value of the natural frequency that is equal to the natural frequency at a zero flow state of the tube. Based on the approximate solution to Housner's equation presented above and experimental confirmation, the change in the frequency of oscillation of the flowmeter due to the changes in the mass flow rate is set forth below:

$$\omega = \frac{\omega_n^*}{(1 - MR\ VR\ K_\rho)}$$

where
$\omega$ = the corrected natural frequency of the material filled flow tube which is the calculated no flow natural frequency;
$\omega^*$ = the measured natural frequency of the material filled flow tube;
MR = the measured mass flow rate of the material
VR the measured volume flow rate of the material $$VR = \frac{MR}{density}$$

$K_\rho$ = a density coefficient constant =

$$\frac{\omega^* - \omega}{\omega^* (MR)\ VR}$$

This equation can also be stated in terms of the period of the natural frequency.
$T_c = T_m (1 - MR\ VR\ K_\rho)$
$T_c$ = the period corresponding to the corrected natural frequency
$T_m$ = the period corresponding to the measured natural frequency The density coefficient constant is developed by calibrating each flowmeter using two different substances, such as air at zero flow, water at zero flow, and water at flow.

The corrected natural frequency of the material filled flow tube is converted to a tube period that is then used to calculate the density of the material by solving the following equation:

$$D_m = \frac{(d)((tcm)T_c^2 - K_1)}{K_2} + D_a$$

where
d = $D_w - D_a$
$D_w$ = density of water
$D_a$ = density of air
tcm = temp coefficient of tube for measured frequency
$T_c$ = tube period corrected
$K_1 = (tca)T_a^2$
$T_a$ = tube period for air—no flow
tca = temp coefficient of tube for air calibration
$K_2 = (tcw)T_w^2 - tca(T_a)^2$
tcw = temp coefficient of tube for water calibration
$T_w$ = tube period for water—no flow In accordance with the present invention, the output of sensor apparatus connected to or associated with a vibrating flow tube (or tubes) is connected to signal processing circuitry which generates data indicating the measured natural frequency of the vibrating flow tube with material flow, the mass flow rate of the flowing material, as well as the volume flow rate of the flowing material. The signal processing circuitry takes into account the fact that the measured natural frequency does not remain constant with changes in the mass flow rate, but decreases with increased mass flow rates. In so doing, the signal processing circuitry corrects the measured frequency and produces an output specifying a corrected natural frequency corresponding to the zero mass flow rate natural frequency of the vibrating flow tube. This corrected natural frequency is applied to signal processing circuitry which derives an accurate density indication of the material flowing through the flow tube.

BRIEF DESCRIPTION OF THE DRAWING

These and other advantages and features of the invention may be better understood from a reading of the following description thereof taken in conjunction with the drawings in which:

FIGS. 4 and 5 are a flow chart describing the operation of the meter electronics 20 and its microprocessor 236 as it corrects the measured natural frequency and calculates density and other information in accordance with the present invention.

DETAILED DESCRIPTION OF A POSSIBLE PREFERRED EMBODIMENT

One possible preferred exemplary embodiment is illustrated in FIGS. 1 through 6. It is to be expressly understood that the present invention is not to limited to this exemplary embodiment. Other embodiments and modifications are considered to be within the scope of the claimed inventive concept. The present invention can be practiced with other types of meters than the described meter. Successful implementation of the present invention is not dependent on any meter geometry. Also, other linear approximations for providing the corrected natural frequency can be utilized.

Figure 1:
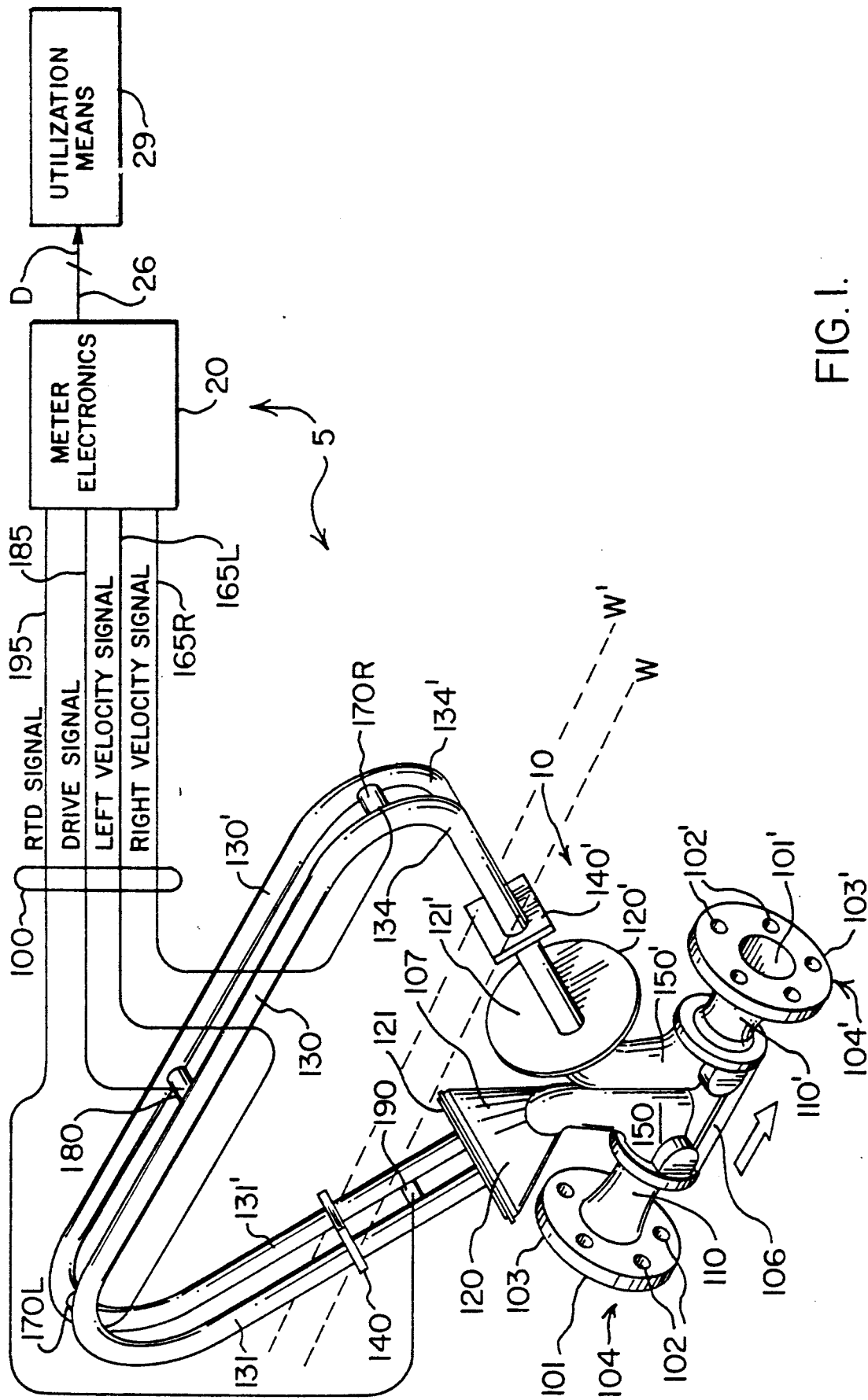
FIG. 1 discloses one possible exemplary embodiment of the invention.

FIG. 1 shows a Coriolis densimeter 5 comprising a Coriolis meter assembly 10 and meter electronics 20. Meter assembly 10 responds to mass flow rate of a process material. Meter electronics 20 is connected to meter assembly 10 via leads 100 so as to enable it to provide density, mass flow rate, volume flow rate and totalized mass flow information to path 26.

Meter assembly 10 includes a pair of manifolds 110 and 110', tubular members 150 and 151', a pair of parallel flow tubes 130 and 130', drive mechanism 180, temperature sensor 190 and a pair of velocity sensors $170_L$ and $170_R$. Flow tubes 130 and 130' have two essentially straight inlet legs 131 and 131' and outlet legs 134 and 134' which converge towards each other at manifold elements 120 and 120'. The flow tube bends at two symmetrical locations along its length and are separated by an essentially straight top middle portion. Brace bars 140 and 140' serve to define the axis W and W' about which each flow tube oscillates.

The side legs 131 and 134 of flow tubes 130 and 130' are fixedly attached to flow tube mounting blocks 120 and 120' and these blocks, in turn, are fixedly attached to elements 150 and 150'. This provides a continuous closed material path through Coriolis meter assembly 10.

When meter 10 having flange 103 having holes 102 is connected, via inlet end 104' and outlet end 101' into a flow tube system (not shown) which carries the process material that is being measured, material enters the meter through an orifice 101 in flange 103 of end 104 of inlet manifold 110 and is conducted through a passageway therein having a gradually changing cross-section to flow tube mounting block 120 having a surface 121. There, the material is divided and routed through flow tubes 130 and 130'. Upon exiting flow tubes 130 and 130', the process material is recombined in a single stream within flow tube mounting block 120' having a surface 121 and is thereafter routed to exit manifold 110'. Within exit manifold 110', the material flows through a passageway having a similar gradually changing cross-section to that of inlet manifold 110 to an orifice 101' in outlet end 104'. Exit end 104' is connected by flange 103' having bolt holes 102' to the flow tube system (not shown).

Flow tubes 130 and 130' are selected and appropriately mounted to the flow tube mounting blocks 120 so as to have substantially the same mass distribution, moments of inertia and elastic modulus about bending axes W—W and W'—W', respectively. These bending axes are located near respective flow tube flanges 140 and 140' and mounting blocks 120 and 120'. The flow tubes extend outwardly from the mounting blocks in an essentially parallel fashion and have substantially equal mass distributions, moments of inertia and elastic modulus about their respective bending axes. Inasmuch as the elastic modulus of the flow tubes changes with temperature, resistive temperature detector (RTD) 190 (typically a platinum RTD device) is mounted to flow tube 130', to continuously measure the temperature of the flow tube. The temperature of the flow tube and hence the voltage appearing across the RTD for a given current passing therethrough is governed by the temperature of the material passing through the flow tube. The temperature dependent voltage appearing across the RTD is used in a well known method by meter electronics 20 to compensate the value of the spring constant for any changes in flow tube temperature. The RTD is connected to meter electronics 20 by lead 195.

Both flow tubes 130 are driven by driver 180 in opposite directions about their respective bending axes W and W' and at what is termed the first out of phase natural frequency of the flowmeter. Both flow tubes 130 and 130' vibrate as the tines of a tuning fork. This drive mechanism 180 may comprise any one of many well known arrangements, such as a magnet mounted to flow tube 130' and an opposing coil mounted to flow tube 130 and through which an alternating current is passed for vibrating both flow tubes. A suitable drive signal is applied by meter electronics 20, via lead 185, to drive mechanism 180.

During oscillation of the flow tubes 130 by drive element 180, the adjacent side legs 131, which are forced closer together than their counterpart side legs 134, reach the end point of their travel where their velocity crosses zero before their counterparts do. The time interval (also referred to herein as the phase difference at a particular frequency, or time difference or simply "Δt" value) which elapses from the instant one pair of adjacent side legs reaches their end point of travel to the instant the counterpart pair of side legs, i.e. those forced further apart, reach their respective end point, is substantially proportional to the mass flow rate of the material flowing through meter assembly 10.

To measure the time interval, Δt, sensors $170_L$ and $170_R$ are attached to flow tubes 130 and 130' near their free ends. The sensors may be of any well-known type. The signals generated by sensors $170_L$ and $170_R$ provide a velocity profile of the complete travel of the flow tubes and can be processed by any one of a number of well known methods to compute the time interval and, in turn, the mass flow of the material passing through the meter.

Sensors 170$_L$ and 170$_R$ produce the left and right velocity signals that appear on leads 165$_L$ and 165$_R$, respectively. Using a time difference measurement provides an accurate way to measure a manifestation of the phase difference that occurs between the left and right velocity sensor signals.

Figure 2:
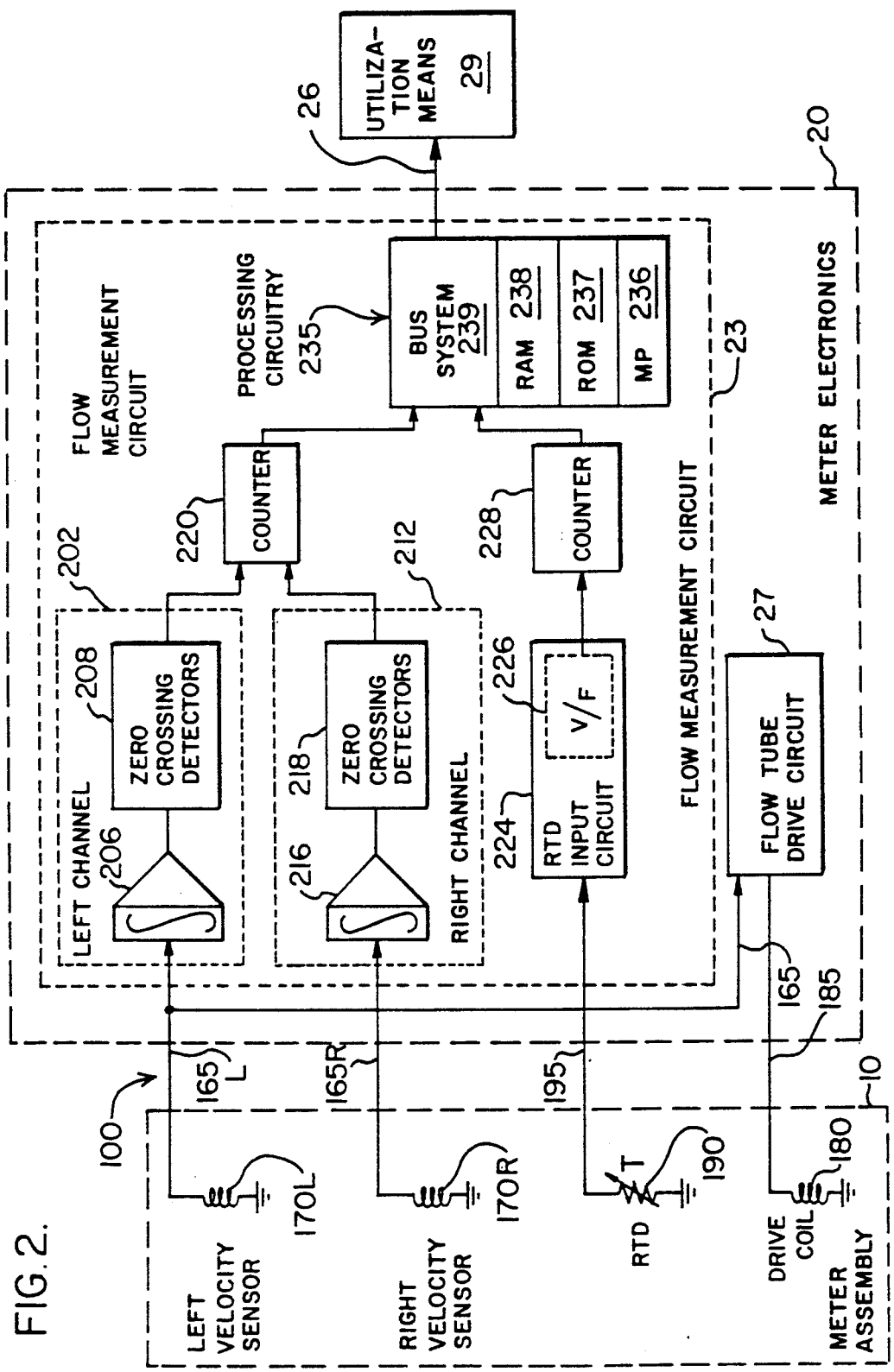
FIG. 2 discloses further details of the meter electronics 20 of FIG. 1.

Meter electronics 20 receives the RTD temperature signal on lead 195, and the left and right velocity signals appearing on leads 165$_L$ and 165$_R$, respectively. Meter electronics 20 produces the drive signal appearing on lead 185 to drive element 180 and vibrate tubes 130 and 130'. Meter electronics 20 processes the left and right velocity signals and the RTD signal to compute the mass flow rate, volume flow rate and the density of the material passing through meter assembly 10. This information is applied by meter electronics 20 over path 26 to utilization means 29. In determining the density, meter electronics 20 corrects the measured natural frequency of tubes 130 and 130' in the manner taught by the present invention and then uses this corrected frequency in its density computation A block diagram of meter electronics 20 is shown in FIG. 2 as comprising flow measurement circuit 23, flow tube drive circuit 27 and processing circuitry 235. Flow tube drive circuit 27 provides a repetitive alternating or pulsed drive signal via lead 185 to drive mechanism 180. Drive circuit 27 synchronizes the drive signal to the left velocity signal on lead 165$_L$ and maintains both flow tubes 130 in opposing sinusoidal vibratory motion at their fundamental natural frequency. This frequency is governed by a number of factors, including characteristics of the tubes and the density and mass flow rate of the material flowing therethrough. Since circuit 27 is known in the art and its specific implementation does not form any part of the present invention, it is not discussed herein in further detail. The reader is illustratively referred to U.S. Pat. Nos. 5,009,109 (issued to P. Kalotay et al. on Apr. 23, 1991); 4,934,196 (issued to P. Romano on Jun. 19, 1990) and 4,876,879 (issued to J. Ruesch on Oct. 31, 1989) for a further description of different embodiments for the flow tube drive circuit.

Flow measurement circuit 23 including processing circuitry 235 which processes the left and right velocity signals on leads 165$_L$ and 165$_R$, respectively, along with the RTD signal on lead 195, in a well known manner, to calculate the mass flow rate and volume flow rate of the material passing through meter assembly 10. Output information is applied over path 26 to utilization means 29 which may be either a display or a process control system. Processing circuitry 235 also operates in accordance with the present invention to measure the natural frequency of tubes 130, to correct this frequency, and to use this corrected frequency in deriving highly accurate density information.

Inasmuch as the method by which flow measurement circuit 23 generates mass flow rate and volume flow rate is well known to those skilled in the art, only that portion of electronics 20 that is germane to the present invention is discussed below. Measurement circuit 23 contains two separate input channels: left channel 202 and right channel 212. Each channel contains an integrator and two zero crossing detectors. Within both channels, the left and right velocity signals are applied to respective integrators 206 and 216, each of which effectively forms a low pass filter. The outputs of these integrators are applied to zero crossing detectors (effectively comparators) 208 and 218, which generates level change signals whenever the corresponding integrated velocity signal exceeds a voltage window defined by a small predefined positive and negative voltage level, e.g. ±2.5 V. The outputs of both zero crossing detectors 208 and 218 are fed as control signals to counter 220 to measure a timing interval, in terms of clock pulse counts, that occurs between corresponding changes in these outputs. This interval is the $\Delta t$ value and varies with the mass flow rate of the process material. This $\Delta t$ value, in counts, is applied in parallel as input data to processing circuitry 235.

Temperature element RTD 190 is connected by path 195 to an input of RTD input circuit 224 which supplies a constant drive current to the RTD element 190, linearizes the voltage that appears across the RTD element and converts this voltage using voltage/frequency (V/F) converter 226 into a stream of pulses that has a scaled frequency which varies proportionally with any changes in RTD voltage. The resulting pulse stream produced by circuit 224 is applied as an input to counter 228 which periodically counts the stream and produces a signal, in counts, that is proportional to the measured temperature. The outputs of counter 228 is applied as input data to processing circuit 235. Processing circuit 235, which is advantageously a microprocessor based system, determines the mass flow rate from the digitized $\Delta t$ and temperature values applied thereto. The digitized temperature value is used to modify a meter factor value based upon the temperature of the flow tubes. This compensates for changes in flow tube elasticity with temperature. The meter factor, as modified, (i.e. a temperature compensated meter factor—RF) is then used to calculate the mass flow rate and volume flow rate from the measured $\Delta t$ value and calculated density value. Having determined the mass flow rate and volume flow rate, circuitry 235 then updates output signals over leads 26 to utilization means 29.

Processing circuitry 235 on FIG. 2 includes microprocessor 236 and memory elements including a ROM memory 237 and a RAM memory 238. The ROM 237 stores permanent information that is used by microprocessor 236 in performing its functions while RAM memory 238 stores temporary information used by microprocessor 236. The microprocessor together with its ROM and RAM memories and bus system 239 control the overall functions of the processing circuitry 235 so that it can receive the signals from counters 220 and 228 and process them in the manner required to apply, over path 26 to utilization means 29, the various items of data the Coriolis effect densimeter of the present invention generates.

Some of this information is the mass flow rate information and volume flow rate information. Processing circuitry 235, including microprocessor 236 together with memory elements 237 and 238, operate in accordance with the present invention to provide highly accurate density information over a wide range of mass flow rates of the material flowing through vibrating tubes 130. As subsequently described in detail in connection with the flow charts of FIGS. 4 and 5, this highly accurate density information is derived by the steps of measuring the natural frequency of the vibrating tubes from the signals provided by the velocity sensors 170, correcting this measured natural frequency to compensate for the fact that the measured natural frequency of tubes 130 decreases with increasing mass flow rates therethrough, and using this corrected frequency in a density calculation to derive highly accurate density output data. This density output data is of far greater accuracy than would be the case if the measured natural frequency, rather than the corrected natural frequency, were used in the density calculation.

Figure 6:
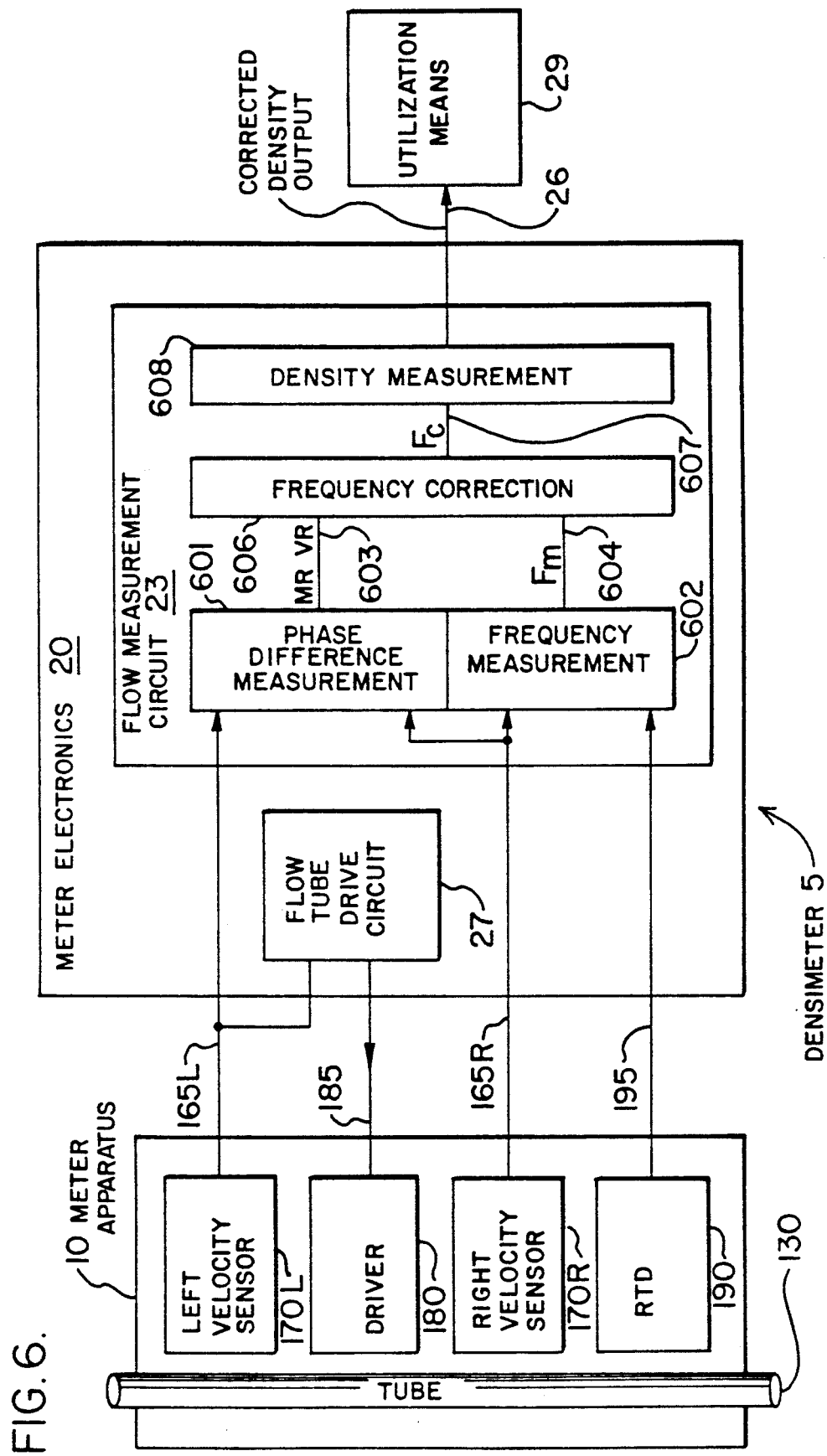
FIG. 6 comprises a simplified portrayal of FIG. 2.

FIG. 6 discloses the invention of FIG. 2 in simplified form. Corresponding elements on FIGS. 2 and 6 have identical reference numbers to facilitate an understanding of the system of FIG. 6. FIG. 6 discloses the densimeter as comprising meter apparatus 10 on the left which includes flow tube 130, the left velocity sensor 170L, the right velocity sensor 170R, driver 180, and RTD temperature sensor 190. These elements are connected over paths 165L, 185, 165R, and 195 to meter electronics 20. These elements perform the same functions as already described in connection with FIG. 2. Meter electronics 20 comprises the flow tube drive circuit 27 and the flow measurement circuit 23 which function as described in connection with FIG. 2 to receive and send signals to and from meter apparatus 10. Meter electronics 20 receives these signals and generates high accuracy density information for the material flowing in vibrating tube 130.

The flow measurement circuit 23 is shown in simplified form on FIG. 6 and comprises a phase difference measurement circuit 601 and a frequency measurement circuit 602. Phase difference measurement circuit receives over path 165L and 165R the output of the left and right sensors, and, in response thereto, generates various information including the mass flow rate MR and volume flow rate VR of the material currently flowing within tube 130. This MR and VR information is applied over path 603 to frequency correction element 606. Frequency measurement circuit 602 receives the temperature information over path 195 and the output signal of the right velocity sensor 170R over path 165R. In response to the receipt of this information, frequency measurement circuit generates an output $F_m$ indicating the measured resonant frequency of vibrating tube 130 as material flows therethrough. This output signal $F_m$ is applied over path 604 to the frequency correction circuit 606. Frequency correction circuit 606 responds to the reception of the mass flow rate MR, the volume flow rate VR, and the measured frequency $F_m$ and generates a corrected frequency output signal $F_c$ which corrects the measured frequency $F_m$ to compensate for the fact that the measured frequency $F_m$ differs from the no flow natural frequency of the tube 130 because of the mass flow rate of the material currently flowing within tube 130.

Corrected frequency $F_c$ is applied together with other information not shown on FIG. 6 to density measurement element 608 which generates accurate density information for the material currently flowing within tube 130. The density information generated by density measurement element 608 is of greater accuracy at large mass flow rate conditions because it uses the corrected frequency $F_c$ rather than the measured frequency $F_m$ in its density computations.

The output signal of density measurement element 608 is applied over path 26 to utilization means 29 which may either comprise a meter for a visual display of the generated density information or, alternatively, may comprise a process control system that is controlled by the density signal on path 26.

Figure 3:
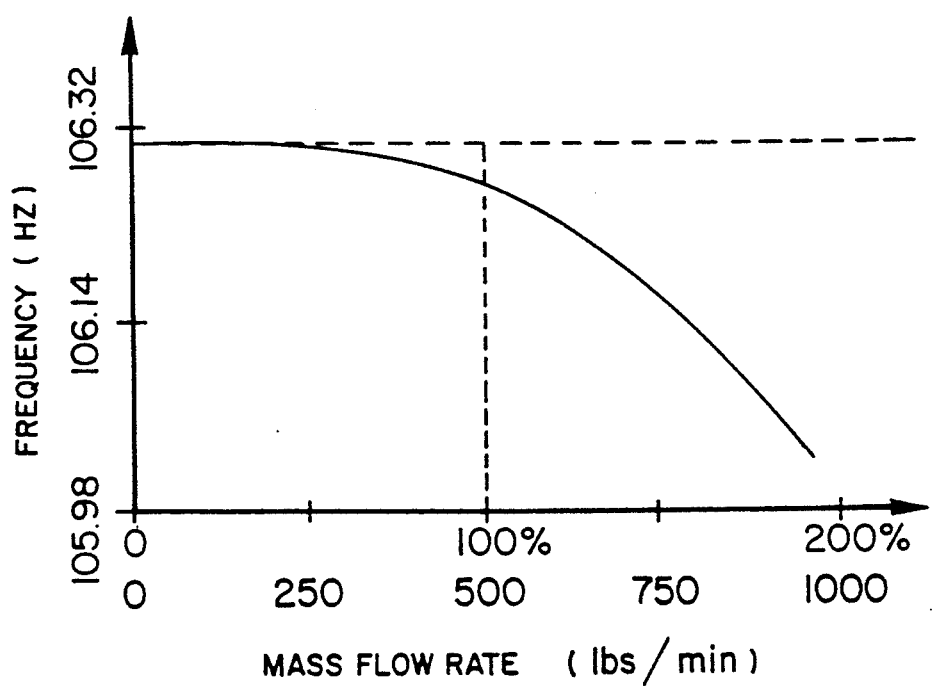
FIG. 3 is a curve illustrating the decreasing natural frequency/mass flow rate relationship of a Coriolis meter.

As illustrated in FIG. 3, the natural frequency of an oscillating tube decreases as the mass flow rate of the material flowing through the tube increases. The data in FIG. 3 is representative of this effect for a given flow tube geometry and a flowing material having constant density. The actual slope of the curve will change for different flow tube geometries and densities of fluids and is easily ascertained by developing the constant K3, discussed above. The vertical axis of FIG. 3 corresponds to the first out of phase natural frequency of the flowmeter. The horizontal axis is labeled in pounds per minute (lbs/min) of mass flow rate. The percentages are included to represent the commercially recommended and useable flow range of the preferred embodiment. The 100% point is the recommended operating range but the flowmeter may be operated up to the 200% point if the user is not concerned with the resulting pressure drop across the meter. In the initial portion of the curve at low mass flow rates, the natural frequency remains relatively constant. However as the mass flow rate increases towards and beyond the 100% rate, the natural frequency decreases. This is the effect that the present invention corrects so that an accurate measurement of the density of the flowing material can be determined. The operation of the present invention in correcting the natural frequency for this effect is shown in FIGS. 4 and 5.

Figure 5:
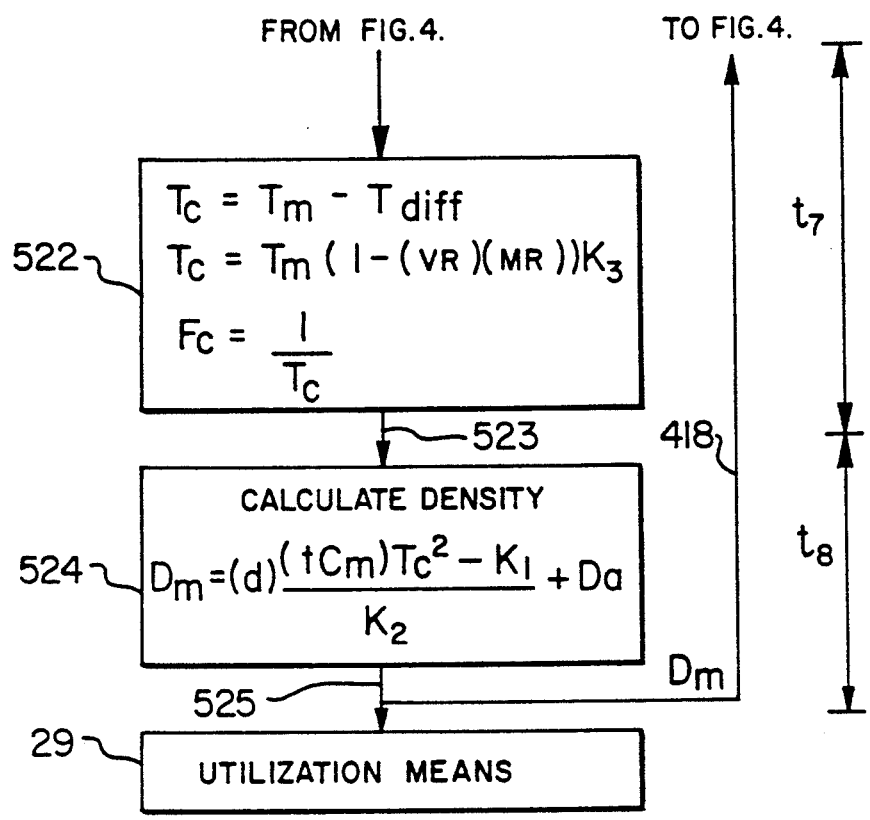

FIGS. 4 and 5 describe in flow chart form how microprocessor 236 and memories 237 and 238 operate in computing a corrected natural frequency of vibrating tubes 130 as well as the density of the material flowing through the tubes. This computation is done in a series of sequential time intervals $t_1$—$t_8$ shown on the right side of FIGS. 4 and 5. The process begins in element 404 in which microprocessor 236 receives input and setup information over paths 401, 402, 403 and 405. This is done in time interval $t_1$. The pickoff signal RPO from the right velocity sensor $170_R$ is applied to the microprocessor over path 401. The pickoff signal LPO from the left velocity sensor $170_L$ is applied over path 402. The temperature signal RTD is applied over path 403 and information representing constants $K_1$, $K_2$, $K_3$ is applied from memories 237 and 238 over path 405. The information received by element 404 is applied during time interval $t_2$ over path 406 to element 407 which determines the $\Delta t$ or $\Delta$ phase at a given frequency information which, as previously described, represents the primary influence of the Coriolis forces as material flows through the vibrating tubes. Signal 406 is also applied to element 408 which measures the frequency of the output signals of sensor elements 170. The output of element 408 is a signal representing the measured natural frequency of tubes 130 with material flow. This signal is applied over path 410 to element 419. The function of this element is subsequently described.

The $\Delta t$ or $\Delta$ phase at a given frequency information generated by element 407 is applied during time interval $t_3$ over path 415 to element 409 which filters this information to remove noise and undesired frequency components. The output of element 409 is applied during interval $t_3$ over path 411 to element 412 which subtracts the mechanical zero offset of the structure associated with tubes 130 from the $\Delta t$ signal provided to path 411. The output of element 412 is a corrected $\Delta t$ signal which is applied over path 413 to element 414 during interval $t_4$ which converts the $\Delta t$ signal to a mass flow rate representation of the flowing material. This mass flow rate may be expressed in terms of grams per second. The output of element 414 representing the mass flow rate is applied during interval $t_3$ over path 416 to element 417 which calculates the volume flow rate of the flowing material by dividing the mass flow rate by the material density from the previous measurement cycle as feedback over path 418 from element 524. The operation of element 524 is subsequently described. The output of element 417 is the mass flow rate and volume flow rate information and is applied over path 420 to element 419.

Element 419 receives the mass flow rate and volume flow rate information over path 418 during interval $t_6$ and additionally receives the measured natural frequency over path 410 from element 408. In response to the receipt of this information, element 419 computes a differential frequency $F_c$ and a differential period $T_{diff}$ corresponding to the differential frequency $F_c$. This differential frequency $F_c$ represents the amount by which the measured natural frequency on path 410 must be corrected to ascertain the corrected natural frequency of vibrating tube 130. This corrected natural frequency is equal to the zero mass flow rate natural frequency of the tube. As previously described, this correction is necessary because of the relationship between the natural frequency and mass flow rate indicated in FIG. 3 wherein it is shown that the measured natural frequency decreases as mass flow rate increases. This frequency differential or correction is calculated by element 419 by multiplying the period $T_m$ of the measured frequency by the volume flow rate (VR) and by the mass flow rate (MR) and by constant $K_3$. This relationship is shown in element 419 in terms of the tube period rather than the tube frequency. However, as is well-known, the tube period and natural frequency bear a reciprocal relationship to one another with the period being equal to a constant divided by the frequency. The constant $K_3$ is equal to the tube period for a flow state minus the tube period at a no flow state divided by the $T_{FLOW}$(the tube period$_{flow}$) (MR)(VR). This expression is $$K_3 = \frac{T_{FLOW} - T_{NO\ FLOW}}{(T_{FLOW})\ (MR)\ (VR)}$$

Element 419 applies an output signal representing the period of the calculated frequency differential over path 421 to element 522 during period $t_7$ which calculates a corrected tube frequency $F_c$ and a corrected tube period $T_c$. This corrected tube period $T_c$ corresponds to the corrected natural frequency $F_c$ and is determined by combining the period $T_M$ of the measured frequency with the differential period $T_{diff}$ corresponding to the differential frequency calculated by element 419. The relationship wherein the differential period $T_{diff}$ is combined with the measured period $T_m$ is $T_c = T_M(1-(VR)(MR))K_3$.

Element 522 applies an output signal representing the corrected natural frequency of tubes 130 over path 523 to element 524 which, during interval $t_8$, calculates the density of the flowing material using the corrected frequency (period) information derived by element 522. The expression used by element 524 to perform this calculation is $$D_m = \frac{(d)\ ((tcm)T_c^2 - K_1)}{K_2} + D_a$$

where
$d = D_w - D_a$
$D_w$ = density of water
$D_a$ = density of air
tcm = temp coefficient of tube for measured frequency
$T_c$ = tube period corrected
$K_1 = (tca)T_a^2$
$T_a$ = tube period for air—no flow
tca = temp coefficient of tube for air calibration
$K_2 = (tcw)T_w^2 - tca(T_a)^2$
tcw = temp coefficient of tube for water calibration
$T_w$ = tube period for water—no flow The density information generated by element 524 is applied as feedback information over path 525 and path 418 to element 417 which calculates a material volume flow rate of improved precision using both the density information and the mass flow rate information as inputs. The density information on path 425 is also extended to the utilization means 29.

It is to be expressly understood that the claimed invention is not to be limited to the description of the preferred embodiment but encompasses other modifications and alterations within the scope and spirit of the inventive concept.

For example, the physical embodiment of the vibrating Coriolis effect tube structure need not be as shown herein on FIG. 1 wherein it is portrayed as a pair of substantially U-shaped tubes. This need not be the case and, if desired, a single vibrating U-tube may be used. Also, if desired, any vibrating tube densimeter, such as a straight tube Coriolis effect structure may be used. Also, the description herein has described a sensor structure comprising a pair of sensors with the sensor outputs being used to derive what is herein termed as Δt information which is used by processing circuitry to generate the mass flow rate, volume flow rate and other information required to generate the output data for which the Coriolis meter is designed to provide. This Δt technique need not be used and, as is well-known in the art, an amplitude sensor may be used wherein the magnitude of the Coriolis effect is proportional to the magnitude of the signal output of the sensor. This magnitude along with other information is then used to derive the mass flow rate, volume flow rate and other information the meter is to provide.

In summary, the principles of the present invention are not limited for use with a double U-tube structure as shown. They may also be used with a single U-tube, a substantially straight vibrating tube or of any other suitable tube structure known in the art. Furthermore, the invention is not limited to its use in connection with Δt type signal processing, but instead, may be used in systems where the Coriolis force is expressed in terms of an amplitude signal.

Further, the material whose density is determined by the method and apparatus of the present invention may include a liquid, a gas, a mixture thereof, as well as any substance that flows such as slurries of different types. The mass flow rate (MR) and volume flow rate (VR) of the flowing material may be generated by the apparatus comprising the densimeter or, alternatively, can be generated by separate apparatus and applied to the densimeter of the present invention.

We claim:

1. A method of operating an apparatus for ascertaining the density of material flowing through a meter having at least one vibrating tube whose natural frequency decreases as the mass flow rate of material through said tube increases, said method comprising the steps of:

measuring the natural frequency of said vibrating tube as said material flows therethrough, generating a signal representing a corrected natural frequency of said tube in response to said measurement of said natural frequency, wherein said corrected natural frequency is greater than said measured natural frequency by the amount by which said measured natural frequency is decreased from said corrected natural frequency by said material mass flow rate through said tube, and generating an output signal specifying the density of said material flowing through said tube in response to the generation of said signal representing said corrected natural frequency.

2. The method of claim 1 wherein said measured natural frequency is decreased from a zero mass flow rate natural frequency of said tube by said material mass flow rate through said tube.

3. The method of claim 2 wherein said method further comprises the step of measuring the mass flow rate of said material through said tube; and wherein said step of generating said signal representing said corrected natural frequency comprises the step of generating said signal representing said corrected natural frequency in response to said measurement of said mass flow rate.

4. The method of claim 3 wherein said method further comprises the step of measuring the volume flow rate of said material through said tube; and wherein said step of generating said signal representing said corrected natural frequency further comprises the step of generating said signal representing said corrected natural frequency in response to said measurement of said volume flow rate.

5. The method of claim 4 wherein said output signal specifying said density is applied as a feedback signal to generate said volume flow rate measurement.

6. The method of claim 1 wherein said step of generating said signal representing said corrected natural frequency includes the steps of:

determining a differential tube period corresponding to a differential tube natural frequency equal to the amount by which said measured natural frequency is reduced in magnitude from said corrected natural frequency by said mass flow rate of material in said tube, and combining said differential tube period and a tube period corresponding to said measured natural frequency to obtain a corrected tube period corresponding to said corrected natural frequency.

7. The method of claim 6 wherein said step of determining a differential tube period comprises the steps of:

multiplying said tube period corresponding to said measured natural frequency by the expression (MR)(VR)K where MR is said mass flow rate of said material, where VR is said volume flow rate of said material, and where K is a constant of said meter.

8. The method of claim 6 wherein said step of determining said differential tube period comprises the steps of:

measuring said mass flow rate MR of said material,
measuring the volume flow rate VR of said material,
specifying a constant K of said meter and
multiplying said tube period corresponding to said measured natural frequency by the expression $(MR \times VR \times K)$.

9. The method of claim 1 wherein said method further comprises the steps of:

oscillating said tube about an axis, measuring a movement of said tube for generating a second signal indicating the Coriolis force on said tube caused by said oscillation and said material flow, measuring the mass flow rate MR of said material in response to said generation of said second signal, measuring the volume flow rate VR of said material in further response to said generation of said second signal, supplying a third signal representing a constant K of said meter specifying the expression $(1 - MR \times VR \times K)$, and multiplying a tube period corresponding to said measured natural frequency of said tube by said expression to obtain a corrected tube period corresponding to said corrected natural frequency.

10. The method of operating an apparatus for ascertaining the density of material flowing through a Coriolis effect densimeter having at least one vibrating tube, said method comprising the steps of:

generating a first signal indicating a measured natural frequency of said tube as material flows therethrough, generating a second signal representing a tube period corresponding to a differential natural frequency of said tube as said material flows therethrough, said second signal representing a correction factor specifying the amount by which said measured natural frequency of said tube decreases with an increase in the mass flow rate of said material through said tube, generating a third signal representing a corrected tube period corresponding to a zero material mass flow rate natural frequency of said tube by combining the tube period corresponding to said measured natural frequency indicated by said first signal and said tube period corresponding to said differential frequency indicated by said second signal, and generating an output signal indicating the density of said material in response to said generation of said third signal representing said tube period corresponding to said zero material mass flow rate natural frequency.

11. The method of claim 10 wherein said density of said material is determined by solving the expression $$D_m = \frac{(d)(tcm)T_c^2 - K_1}{K_2} + D_a$$

where
$D_m$ = density of said material,
$d = D_w - D_a$,
$D_w$ = density of water,
$D_a$ = density of air,
$tcm$ = temp coefficient of tube for measured frequency,
$T_c$ = tube period corrected,
$K_1 = (tca)T_a^2$,
$T_a$ = tube period for air—no flow,
$tca$ = temp coefficient of tube for air calibration,
$K_2 = (tcw)T_w^2 - tca(T_a)^2$,
$tcw$ = temp coefficient of tube for water calibration, and
$T_w$ = tube period for water—no flow.

12. The method of claim 10 wherein said step of generating said second signal representing said tube period corresponding to said differential natural frequency comprises the steps of:

measuring the mass flow rate MR of said material, measuring the volume flow rate VR of said material, specifying a constant K of said densimeter, and multiplying said tube period corresponding to said measured natural frequency by the factor (MR×VR×K).

13. The method of claim 10 wherein said step of generating said second signal representing said differential tube period comprises the steps of:

multiplying said tube period corresponding to said measured natural frequency by the expression (MR)(VR)K where MR is said mass flow rate of said material, where VR is said volume flow rate of said material, and where K is a constant of said densimeter.

14. The method of claim 10 wherein said method further comprises the steps of:

oscillating said tube about an axis, measuring a movement of said tube for generating a second signal indicating the Coriolis force on said tube caused by said oscillation and said material flow, measuring the mass flow rate of said material in response to said generation of said second signal, measuring the volume flow rate of said material in further response to said generation of said second signal, supplying a signal representing a constant K of said densimeter;

specifying the expression (1−MR×VR×K) where MR is said mass flow rate and where VR is said volume flow rate and where K is a constant of said densimeter, and multiplying said tube period corresponding to said measured natural frequency by said expression to obtain said corrected tube period corresponding to said zero material mass flow rate natural frequency.

15. A method of operating an apparatus for ascertaining the density of material flowing through a Coriolis effect densimeter having at least one vibrating tube whose natural frequency of said tube decreases as the mass flow rate through said tube increases, said method comprising the steps of:

measuring the natural frequency of said tube as said material flows therethrough, in response to said measurement of said natural frequency, generating a natural frequency correction factor to offset said measured natural frequency by the amount by which said measured frequency is reduced by said mass flow rate, generating a signal representing a corrected natural frequency of said tube in response to said generation of said correction factor, and generating an output signal indicating the density of said material flowing through said tube in response to said generation of said signal representing corrected natural frequency.

16. The method of claim 15 wherein said step of generating said signal representing said corrected natural frequency includes the steps of:

determining a tube period corresponding to a differential frequency equal to the amount by which said measured natural frequency is reduced in magnitude from a zero mass flow rate natural frequency by said mass flow rate of said material in said tube, and combining said tube period corresponding to said differential natural frequency and a tube period corresponding to said measured natural frequency to obtain a tube period corresponding to said corrected natural frequency.

17. The method of claim 16 wherein said step of determining a tube period corresponding to said differential natural frequency comprises the steps of:

multiplying said tube period corresponding to said measured natural frequency by the expression (MR)(VR)K where MR is said mass flow rate of said material, where VR is said volume flow rate of said material, and where K is a constant of said densimeter.

18. The method of claim 16 wherein said method further comprises the steps of:

oscillating said tube about an axis, measuring a movement of said tube for generating a second signal indicating the Coriolis force on said tube caused by said oscillation and said material flow, measuring the mass flow rate of said material in response to said generation of said second signal, measuring the volume flow rate of said material in further response to said generation of said second signal, supplying a signal representing a constant K of said densimeter, specifying the expression (1−MR×VR×K) where MR is said mass flow rate and where VR is said volume flow rate, and multiplying said tube period corresponding to said measured natural frequency by said expression to obtain said tube period corresponding to said corrected natural frequency.

19. A method of operating an apparatus for ascertaining the density of material flowing through at least one vibrating tube of a Coriolis effect densimeter, said method comprising the steps of:

measuring the natural frequency of said tube as material flows therethrough, measuring the mass flow rate MR of said flowing material, measuring the volume flow rate VR of said flowing material, specifying a constant K for said densimeter, specifying expression (1−MR×VR×K), generating a signal representing a tube period corresponding to a zero mass flow rate natural frequency of said tube by multiplying a tube period corresponding to said measured natural frequency by said expression, and generating an output signal indicating said density of said material in response to said generation of said tube period corresponding to said zero mass flow rate natural frequency.

20. A method of operating apparatus comprising a Coriolis effect densimeter for ascertaining the density of material flowing through at least one tube of said densimeter, said method comprising the steps of:

vibrating said tube as said material flows therethrough, operating sensor means affixed to said tube for generating an output signal representing the magnitude of the Coriolis forces generated on said tube as a result of said material flow and said vibration, measuring the natural frequency of said tube as material flows therethrough in response to the generation of said output signal, processing said output signal to determine the mass flow rate MR of said flowing material, processing further said output signal to determine the volume flow rate VR of said flowing material, specifying a constant K for said densimeter, specifying the expression $(1-MR \times VR \times K)$, obtaining a corrected tube period corresponding to a zero mass flow rate natural frequency of said tube by multiplying a tube period corresponding to said measured flow natural frequency by said expression, generating information specifying the density of said material by solving the expression $$D_m = \frac{(d)(tcm)T_c^2 - K_1}{K_2} + D_a$$

where $Dm$ = density of said material, $d = D_w - D_a$, $D_w$ = density of water, $D_a$ = density of air, tcm = temp coefficient of tube for measured frequency, $T_c$ = tube period correction, $K_1 = (tca)T_a^2$, $T_a$ = tube period for air—no flow, tca = temp coefficient of tube for air calibration, $K_2 = (tcw)T_w^2 - tca(T_a)^2$, tcw = temp coefficient of tube for water calibration, and $T_w$ = tube period for water—no flow, to obtain said density of said material, and applying said density information to a utilization means for further processing.

21. A method of operating apparatus comprising a Coriolis effect densimeter for ascertaining the density of material flowing through at least one vibrating tube of said densimeter, said densimeter having a natural frequency of said tube that decreases with increases in the material mass flow rate through said tube, said method comprising the steps of:

vibrating said tube as said material flows therethrough, operating sensor means affixed to said tube to generate a signal indicating the magnitude of the Coriolis forces generated on said tube as a result of said $ flow and said vibration, measuring the natural frequency of said tube as material flows therethrough in response to said generation of said signal, measuring the mass flow rate (MR) of said flowing material in response to said generation of said signal, measuring the volume flow rate (VR) of said flowing material in further response to said generation of said signal, specifying a constant K for said densimeter, specifying the expression $(1-MR \times VR \times K)$, obtaining a corrected tube period corresponding to a zero flow rate natural frequency of said tube by dividing a tube period corresponding to said measured natural frequency by said expression, and generating information specifying said density by solving the expression $$D_m = \frac{(d)(tcm)T_c^2 - K_1}{K_2} + D_a$$

where $d = D_w - D_a$, $D_w$ = density of water, $D_a$ = density of air, tcm = temp coefficient of tube for measured frequency, $T_c$ = tube period corrected, $K_1 = (tca)T_a^2$, $T_a$ = tube period for air—no flow, tca = temp coefficient of tube for air calibration, $K_2 = (tcw)T_w^2 - tca(T_a)^2$, tcw = temp coefficient of tube for water calibration, and $T_w$ = tube period for water—no flow, to obtain said density of said material, and applying said density information to a utilization means for further processing.

22. A method for ascertaining the density of material flowing through a flow tube vibrating at the natural frequency of said flow tube, said method comprising the steps of:

measuring the natural frequency of said flow tube during a first time interval;

measuring the mass flow rate of said material through said flow tube during a second time interval;

generating during a third time interval a signal representing said natural frequency measured during said first time interval corrected for changes in the mass flow rate measured during said second time interval; and generating during a fourth time interval information specifying the density of said material in response to the generation of said signal representing said corrected natural frequency.

23. The method of claim 22 wherein said method further includes the steps of:

measuring in an intermediate time interval the volume flow rate of said material flowing through said flow tube;

specifying prior to said first time interval a calibration constant for said flow tube; and generating said signal representing said corrected natural frequency according to the mass flow rate measured in said second time interval, the natural frequency measured in said first time interval, the volume flow rate determined in said intermediate time interval and said calibration constant.

24. The method of claim 23 wherein said step of generating said signal representing said corrected natural frequency generates said corrected natural frequency based on the equation:

where:

$$\omega_n = \frac{\omega_n^*}{1 - MR\ VR\ K}$$

$\omega_n$ = said corrected natural freq., $\omega_n^*$ = said measured natural frequency, MR = said mass rate of said material, VR = said volume flow rate of said material, and K = said calibration constant of said flow tube.

25. A system for ascertaining the density of material flowing through a flow tube, said system comprising:

means for driving said flow tube at the natural frequency of said flow tube;

means for measuring said natural frequency of said driven flow tube;

means for measuring the mass flow rate of material flowing through said flow tube;

means for indicating changes in said natural frequency of said flow tube due to changes in the mass flow rate of said material in said flow tube; and means responsive to said measurement by said means for measuring said natural frequency and to said indication by said means for indicating changes in said natural frequency due to changes in said mass flow rate for ascertaining the density of said material in said flow tube.

26. The method of claim 25 wherein said means for indicating changes in said natural frequency due to changes in said mass flow rate of said material in said flow tube includes:

means responsive to said measurement of said natural frequency and to said measurement of said mass flow rate for generating a signal representing said natural frequency measured by said frequency measuring means corrected for changes in said measured natural frequency due to changes in said mass flow rate.

27. The method of claim 26 wherein said system further includes:

means for measuring the volume flow rate of said material; and where said means for indicating changes of said natural frequency includes said means for generating said signal representing said corrected natural frequency according to the following equation:

$$\omega_n = \frac{\omega_n^*}{1 - MR\ VR\ K}$$

where:

$\omega_n$ = said corrected natural freq.,
$\omega_n^*$ = said measured natural frequency,
MR = said mass rate of said material,
VR = said volume flow rate of said material, and
K = said calibration constant for said flow tube.

28. An apparatus for ascertaining the density of material flowing through a vibrating flow tube, said apparatus comprising:

means for measuring the natural frequency of said flow tube during a first time interval;

means for measuring the mass flow rate of said material through said flow tube during a second time interval;

means responsive to said measurement of said natural frequency and to said measurement of said mass flow rate for generating during a third time interval a signal representing the tube period corresponding to said measured natural frequency corrected for changes in said mass flow rate measured during said second time interval; and means responsive to said generating of said signal representing said period corresponding to said corrected natural frequency for generating during a fourth time interval information specifying the density of said material based on said period corresponding to said corrected natural frequency.

29. The method of claim 28 wherein said apparatus further includes:

means for indicating in an intermediate time interval the volume flow rate of said material flowing through said flow tube;

means for specifying a calibration constant for said flow tube determined prior to said first time interval; and wherein said means for generating said signal representing said tube period corresponding to said corrected natural frequency determines said period corresponding to said corrected natural frequency according to said mass flow rate measured in said second time interval, and said natural frequency measured in said first time interval, and said volume flow rate measured in said intermediate time interval and said calibration constant.

30. The apparatus of claim 29 wherein said means for generating said signal representing said period corresponding to said corrected natural frequency determines said period corresponding to said measure natural frequency according to the following equation:

$$T_c = T_m(1 - MR\ VR\ K)$$

where $T_c$ = said period corresponding to said corrected natural freq.,
$T_m$ = said period of said measured natural frequency,
MR = said mass rate of said material,
VR = said volume flow rate of said material, and
K = said calibration constant of said flow tube.

31. An apparatus for ascertaining the density of material flowing through a meter having at least one vibrating tube whose natural frequency decreases as the mass flow rate of material through said tube increases, said apparatus comprising:

apparatus for measuring the natural frequency of said vibrating tube as said material flows therethrough, apparatus for generating a signal representing a corrected natural frequency of said vibrating tube in response to said measurement of said natural frequency wherein said corrected natural frequency is greater than said measured natural frequency by the amount by which said measured natural frequency is decreased from said corrected natural frequency by the material mass flow rate through said tube, and apparatus for generating an output signal specifying the density of said material flowing through said tube in response to said generation of said signal representing said corrected natural frequency.

32. The apparatus of claim 31 wherein said measured natural frequency is decreased from a zero mass flow rate natural frequency by said material mass flow rate of said tube.

33. The apparatus of claim 32 wherein said apparatus further comprises means for measuring the mass flow rate of material through said tube; and wherein apparatus for generating said signal representing said corrected natural frequency comprises apparatus for generating said signal representing said corrected natural frequency in response to said measurement of said mass flow rate.

34. The apparatus of claim 33 wherein said apparatus further comprises apparatus for measuring the volume flow rate of material through said tube, and wherein said apparatus for generating said signal representing said corrected natural frequency further comprises apparatus for generating said signal representing said corrected natural frequency in response to said measurement of said volume flow rate.

35. The apparatus of claim 34 wherein said signal specifying said density is applied as a feedback signal to said means for measuring said volume flow rate to generate said volume flow rate of said material.

36. The apparatus of claim 31 wherein said apparatus for generating said signal representing said corrected natural frequency includes:
apparatus for generating a signal representing a differential tube period corresponding to a differential natural frequency of said tube equal to the amount by which said measured natural frequency is reduced in magnitude by said mass flow rate of material in said tube, and
apparatus for combining said differential tube period and a tube period corresponding to said measured natural frequency to obtain a corrected tube period corresponding to said corrected natural frequency.

37. The apparatus of claim 36 wherein said apparatus for generating said signal representing said differential tube period comprises:
apparatus for multiplying said tube period corresponding to said measured natural frequency by the expression (MR)(VR)K where
MR is said mass flow rate of said material,
where VR is said volume flow rate of said material, and
where K is a constant of said densimeter.

38. The apparatus of claim 36 wherein said apparatus for generating said differential tube period comprises:
apparatus for measuring the mass flow rate MR of said material,
apparatus for measuring the volume flow rate VR of said material,
apparatus for specifying a constant K of said densimeter, and
apparatus for multiplying said tube period corresponding to said measured natural frequency by the expression (MR×VR×K).

39. The apparatus of claim 36 wherein said apparatus further comprises:
apparatus for oscillating said tube about an axis,
apparatus for measuring a movement of said tube for generating a signal indicating the Coriolis force on said tube caused by said oscillation and said material flow,
apparatus for measuring the mass flow rate MR of said material in response to said generation of said signal,
apparatus for measuring the volume flow rate VR of said material in further response to said generation of said signal,
apparatus for supplying a signal representing constant K of said densimeter,
apparatus for generating the expression (1−MR×VR×K), and
apparatus for multiplying said tube period corresponding to said measured natural frequency by said expression to obtain said corrected tube period corresponding to said corrected natural frequency.

40. A Coriolis effect densimeter for ascertaining the density of material flowing through at least one vibrating tube of said densimeter, said densimeter comprising:
apparatus for measuring the natural frequency of said tube as material flows therethrough,
apparatus responsive to said measurement of said natural frequency for generating a signal representing a tube period corresponding to the natural frequency of said tube at a zero mass flow rate of said material by multiplying said tube period corresponding to said measured natural frequency by the expression (1−MR×VR×K) where MR is the mass flow rate of said material,
where VR is the volume flow rate of said material, and
where K is a constant of said densimeter, and
apparatus for generating an output signal indicating the density of said material flowing through said tube in response to said generation of said signal representing said tube period corresponding to said zero mass flow rate natural frequency.

41. An apparatus for ascertaining the density of material flowing through a Coriolis effect densimeter having at least one vibrating tube, said apparatus comprising:
apparatus for generating a first signal representing a measured natural frequency of said tube as material flows therethrough,
apparatus for generating a second signal representing a differential tube period corresponding to a differential natural frequency of said tube as said material flows therethrough, said second signal representing a correction factor specifying the amount by which said measured natural frequency of said tube decreases with an increase in the mass flow rate of said material through said tube,
apparatus for generating a corrected tube period corresponding to a zero material mass flow rate natural frequency of said tube by combining a tube period corresponding to said measured natural frequency indicated by said first signal and said differential tube period corresponding to said differential frequency indicated by said second signal, and
apparatus responsive to said generation of said tube period corresponding to said zero mass flow rate natural frequency for generating an output signal indicating the density of said material.

42. The apparatus of claim 41 wherein said density of said material is generated by solving the expression $$D_m = \frac{(d)(tcm)T_c^2 - K_1}{K_2} + D_a$$

where
$D_m$ = density of said material,
$d = D_w - D_a$,
$D_w$ = density of water,
$D_a$ = density of air,
tcm = temp coefficient of tube for measured frequency,
$T_c$ = tube period correction,
$K_1 = (tca)T_a^2$,
$T_a$ = tube period for air—no flow,
tca = temp coefficient of tube for air calibration,
$K_2 = (tcw)T_w^2 - tca(T_a)^2$,
tcw = temp coefficient of tube for water calibration, and
$T_w$ = tube period for water—no flow.

43. The apparatus of claim 41 wherein said apparatus for generating said second signal representing said differential tube period corresponding to said differential natural frequency comprises:
apparatus for measuring the mass flow rate MR of said material,
apparatus for measuring the volume flow rate VR of said material, apparatus for specifying a constant K of said densimeter, and apparatus for multiplying said tube period corresponding to said measured natural frequency by the factor (MR×VR×K).

44. The apparatus of claim 41 wherein said apparatus for generating said differential tube period comprises:

apparatus for multiplying said tube period corresponding to said measured natural frequency by the expression (MR×VR×K) where MR is said mass flow rate of said material, where VR is said volume flow rate of said material, and where K is a constant of said densimeter.

45. The apparatus of claim 41 wherein said apparatus further comprises:

apparatus for oscillation said tube about an axis, apparatus for measuring a movement of said tube for generating a second signal indicating the Coriolis force on said tube caused by said oscillation and said material flow, apparatus for measuring the mass flow rate of said material in response to said generation of said second signal, apparatus for measuring the volume flow rate of said material in further response to said generation of said signal, apparatus for supplying a signal representing K of said densimeter, apparatus for generating the expression (1−MR×VR×K) where MR is said mass flow rate and where VR is said volume flow rate and where K is a constant of said densimeter, and apparatus for multiplying said tube period corresponding to said measured natural frequency by said expression to obtain said corrected tube period corresponding to said zero material mass flow rate natural frequency.

46. An apparatus for ascertaining the density of material flowing through a Coriolis effect densimeter having at least one vibrating tube whose natural frequency decreases as the mass flow rate through said tube increases, said apparatus comprising:

apparatus for measuring the natural frequency of said tube as said material flows therethrough, apparatus responsive to said measurement of said natural frequency for generating a natural frequency correction factor to offset said measured natural frequency by the amount by which said measured natural frequency is reduced by said mass flow rate, apparatus for generating a signal representing a corrected natural frequency of said tube in response to said generation of said correction factor, and apparatus for generating an output signal representing the density of said material flowing through said tube in response to said generation of said signal representing said corrected natural frequency.

47. The apparatus of claim 46 wherein said apparatus for generating signal representing corrected natural frequency includes:

apparatus for generating a signal representing a tube period corresponding to a differential frequency equal to the amount by which said measured natural frequency is reduced in magnitude from a zero mass flow rate natural frequency by said mass flow rate of said material in said tube, and apparatus for combining said tube period corresponding to said differential natural frequency and a tube period corresponding to said measured natural frequency to obtain a tube period corresponding to said corrected natural frequency.

48. The apparatus of claim 47 wherein said apparatus for generating a signal representing a tube period corresponding to said differential natural frequency comprises:

apparatus for multiplying said tube period corresponding to said measured natural frequency by the expression (MR×VR×K) where MR is said mass flow rate of said material, where VR is said volume flow rate of said material, and where K is a constant of said densimeter.

49. The apparatus of claim 47 wherein said apparatus further comprises:

apparatus for oscillating said tube about an axis, apparatus for measuring a movement of said tube for generating a second signal indicating the Coriolis force on said tube caused by said oscillation and said material flow, apparatus for measuring the mass flow rate of said material in response to said generation of said second signal, apparatus for measuring the volume flow rate of said material in further response to said generation of said second signal, apparatus for supplying a signal representing a constant K of said densimeter, apparatus for generating the expression (1−MR×VR×K) where MR is said mass flow rate and where VR is said volume flow rate, and apparatus for multiplying said tube period corresponding to said measured natural frequency by said expression to obtain said tube period corresponding to said measure natural frequency.

50. An apparatus for ascertaining the density of material flowing through at least one vibrating tube of a Coriolis effect densimeter, said apparatus comprising:

apparatus for measuring the natural frequency of said tube as material flows therethrough, apparatus for measuring the mass flow rate MR of said flowing material, apparatus for measuring the volume flow rate VR of said flowing material, apparatus for specifying a constant K for said densimeter, apparatus for specifying the expression (1−MR×VR×K) when K is a constant, apparatus for generating a signal representing a tube period corresponding to a zero mass flow rate natural frequency of said tube by multiplying a tube period corresponding to said measured natural frequency by said expression, and apparatus for generating an output signal representing said density of said material in response to said generating of said signal representing said tube period corresponding to said zero mass flow rate natural frequency.

51. An apparatus comprising a Coriolis effect densimeter for ascertaining the density of material flowing through at least one tube of said densimeter, said apparatus comprising:

apparatus for vibrating said tube as said material flows therethrough, sensor means affixed to said tube for generating an output signal representing the magnitude of the Coriolis forces generated on said tube as a result of said material flow and said vibration, apparatus for measuring the natural frequency of said tube as material flows therethrough in response to said generation of said output signal of said sensor means, apparatus further responsive to said generation of said output signal for measuring the mass flow rate MR of said flowing material, apparatus further responsive to said generation of said output signal for measuring the volume flow rate VR of said flowing material, apparatus for determining a constant K for said densimeter, apparatus for generating the expression $(1 - MR \times VR \times K)$, apparatus for obtaining a tube period corresponding to a zero mass flow rate natural frequency of said tube by multiplying a tube period corresponding to said measured natural frequency period by said expression, apparatus for generating information specifying the density of said material by solving the expression:

$$D_m = \frac{(d)(tcm)T_c^2 - K_1}{K_2} + D_a$$

where
$D_m$ = density of said material,
$d = D_w - D_a$,
$D_w$ = density of water,
$D_a$ = density of air,
tcm = temp coefficient of tube for measured frequency,
$T_c$ = tube period correction,
$K_1 = (tca)T_a^2$,
$T_a$ = tube period for air—no flow,
tca = temp coefficient of tube for air calibration,
$K_2 = (tcw)T_w^2 - tca(T_a)^2$,
tcw = temp coefficient of tube for water calibration, and
$T_w$ = tube period for water—no flow,
to obtain said density of said material, and apparatus for applying said density information to a utilization means for further processing.

52. A Coriolis effect densimeter for ascertaining the density of material flowing through a pair of substantially U shaped flow tubes of said densimeter, said tube being positioned substantially parallel to each other, said apparatus comprising:

drive means position on said flow tubes, drive circuitry for applying a drive signal to said drive means for vibrating said flow tubes at their natural frequency as said material flows therethrough, sensor means affixed to said flow tubes, said sensor means being responsive to motion imparted to said tubes with respect to each other by the Coriolis forces generated as a result of said vibration of said tubes as said material flows therethrough to generate a signal indicative of the magnitude of the Coriolis forces, apparatus responsive to said generation of said signal for measuring the natural frequency of said flow tubes as material flows therethrough, apparatus further responsive to said generation of said signal indicative of said Coriolis force magnitude to measure the mass flow rate MR of said flowing material, apparatus further responsive to said generation of said signal indicative of said Coriolis force magnitude to measure the volume flow rate VR of said flowing material, apparatus for providing a constant K for said densimeter, apparatus for ascertaining a tube period corresponding to a differential natural frequency by multiplying a tube period corresponding to said measured natural frequency by the expression $(MR \times VR \times K)$, apparatus for generating a signal indicative of a tube period corresponding to a zero mass flow rate natural frequency of said flow tubes with said material therein by combining said tube period corresponding to said measured natural frequency and said tube period corresponding to said differential natural frequency, apparatus responsive to said generating of said signal indicative of said tube period corresponding to said zero mass flow rate natural frequency for generating a signal indicative of the density of said material flowing through said flow tubes, and apparatus for applying said signal indicative of said density to a utilization means and to said means for determining said volume flow rate.

53. The densimeter of claim 52 wherein said signal indicative of said density is generated by solving said expression $$D_m = \frac{(d)(tcm)T_c^2 - K_1}{K_2} + D_a$$

where
$D_m$ = density of said material,
$d = D_w - D_a$,
$D_w$ = density of water,
$D_a$ = density of air,
tcm = temp coefficient of tube for measured frequency,
$T_c$ = tube period correction,
$K_1 = (tca)T_a^2$,
$T_a$ = tube period for air—no flow,
tca = temp coefficient of tube for air calibration,
$K_2 = (tcw)T_w^2 - tca(T_a)^2$,
tcw = temp coefficient of tube for water calibration, and
$T_w$ = tube period for water—no flow.

54. A densimeter for indicating the density of a flowing material in a vibrating tube comprising:

an apparatus including vibrating tube means for carrying said flowing material;

drive means on said apparatus for vibrating said tube at a vibration frequency dependent on the density of said flowing material and the current mass flow rate of said flowing material;

sensing means arranged on said apparatus for providing sensor outputs indicating the frequency of vibration and motion of said tube with said material flow;

means for applying said sensor outputs to a circuit;

means including said circuit responsive to the receipt of said sensor outputs for generating a densimeter output signal indicating the density of said material as a function of the frequency of vibration of said tube; and said circuit including a correction means for correcting the frequency of vibration indicated by said output of said sensors to compensate for a decrease in the frequency of vibration of said tube in response to said material mass flow rate through said tube.

* * * * *